United States Patent
Andersch et al.

(10) Patent No.: US 9,216,929 B2
(45) Date of Patent: Dec. 22, 2015

(54) ALUMINUM OXIDE CERAMICS WITH HYDROXYAPATITE

(75) Inventors: Hans Andersch, Heiningen (DE); Wolfgang Burger, Plochingen (DE); Herbert Richter, Köngen (DE); Gert Richter, Remchingen (DE)

(73) Assignee: Ceram Tec GmbH, Plochingen (DE)

( * ) Notice: Subject to any disclaimer, the term of this patent is extended or adjusted under 35 U.S.C. 154(b) by 0 days.

(21) Appl. No.: 12/072,326

(22) Filed: Feb. 26, 2008

(65) Prior Publication Data

US 2008/0152783 A1    Jun. 26, 2008

Related U.S. Application Data

(63) Continuation of application No. 11/252,377, filed on Oct. 18, 2005, now abandoned, which is a continuation of application No. 10/168,414, filed as application No. PCT/EP00/13109 on Dec. 21, 2000, now abandoned.

(30) Foreign Application Priority Data

Dec. 21, 1999  (DE) .................................. 199 61 917

(51) Int. Cl.
- A61L 27/32 (2006.01)
- B05D 3/12 (2006.01)
- C23C 14/00 (2006.01)
- C04B 41/00 (2006.01)
- A61L 27/42 (2006.01)
- C04B 41/52 (2006.01)
- C04B 41/89 (2006.01)
- C23C 14/14 (2006.01)
- C04B 111/00 (2006.01)

(52) U.S. Cl.
CPC ............. *C04B 41/009* (2013.01); *A61L 27/32* (2013.01); *A61L 27/42* (2013.01); *C04B 41/52* (2013.01); *C04B 41/89* (2013.01); *A61F 2310/00796* (2013.01); *B05D 3/12* (2013.01); *C04B 2111/00836* (2013.01); *C23C 14/14* (2013.01)

(58) Field of Classification Search
CPC ............... A61F 2310/00796; A61F 2/306767; C23C 14/14; B05D 3/12
USPC ................................ 427/2.27, 250, 347, 402
See application file for complete search history.

(56) References Cited

U.S. PATENT DOCUMENTS

| | | | | |
|---|---|---|---|---|
| 4,818,559 A | * | 4/1989 | Hama et al. | 427/2.27 |
| 6,261,322 B1 | * | 7/2001 | Despres et al. | 623/23.53 |
| 6,280,789 B1 | * | 8/2001 | Rey et al. | 427/2.27 |

FOREIGN PATENT DOCUMENTS

| | | | |
|---|---|---|---|
| DE | 4342468 A1 | * | 6/1994 |
| JP | 04242659 A | * | 8/1992 |

* cited by examiner

*Primary Examiner* — Cachet Sellman
(74) *Attorney, Agent, or Firm* — Norton Rose Fulbright US LLP

(57) ABSTRACT

The invention relates to a method for producing hydroxyapatite coated ceramics components. In a first step of the inventive method the ceramic component is provided with a Ti coating and in a second step a hydroxyapatite is applied to the Ti coating. The invention further relates to hydroxyapatite coated ceramic components produced according to the inventive method.

13 Claims, 5 Drawing Sheets

ALUMINUM OXIDE CERAMICS WITH HYDROXYAPATITE

This application is a continuation application of U.S. Ser. No. 11/252,377 filed Oct. 18, 2005, which is a continuation application of U.S. Ser. No. 10/168,414 filed Nov. 12, 2002 (abandoned), incorporated herein by reference in its entirety, which is a §371 of PCT/EP0013109 filed Dec. 21, 2000, which claimed priority from German Patent Application No. 199 61 917.4 filed Dec. 21, 1999.

The subject of the present invention is a method for the manufacture of ceramic components coated with hydroxyapatite, as well as the ceramic components which can be manufactured by this method.

It is known that prostheses which have a hydroxyapatite coating display an especially good ingrowth activity. Care must be taken, however, to see that the hydroxyapatite coating firmly adheres to the prosthesis. In the coating of titanium shafts with hydroxyapatite an especially great strength of adherence can be achieved when the metal surface is given a roughness of $R_a \approx 40\text{-}50$ μm.

The adhesive strength of hydroxyapatite apatite on ceramic surfaces, especially on $Al_2O_3$ ceramics, is not sufficient for the desired use. Thus any direct coating of an aluminum oxide ceramic with hydroxyapatite, such as would be very advantageous for the direct fixation of the femur part of a knee prosthesis, is impossible. Even if the surface roughness is made similar to the roughness of the titanium shafts, the strength of the adhesion of hydroxyapatite is not assured. This has been proven in experiments in which ground and sandblasted samples were used. In comparison with titanium materials the surface roughness of ceramic base materials thus treated is substantially lower. Coating tests with the standard parameters for titanium shafts resulted in no strength of adhesion between hydroxyapatite and aluminum oxide ceramic. Inasmuch as no coating adhered to aluminum oxide bodies under standard conditions, the spray parameters was also modified in the plasma coating apparatus. But even the modified process parameters did not lead to success. The cause of the poor strength of adhesion was determined to be the differences in roughness between the metal and the ceramic. A surface roughness of $R_a \approx 30$ μm cannot be achieved by conventional abrasive methods.

Even methods which lead to increased depth of roughness did not bring the desired success. To produce a greater defined surface roughness, similar specimens were prepared for laser machining under various settings. In this manner it was possible to produce a lasting effect on the surfaces of the $Al_2O_3$ ceramic. While in the case of normal grinding a raw depth of no more than 1 μm could be achieved, the laser treatment succeeded in producing a raw depth of $R_a \approx 9$ μm. FIG. 3 shows the typical surface after the laser treatment. The lasered surface of the aluminum oxide ceramic was then subjected to plasma coating with hydroxyapatite. For the first time a few placed on this surface were detected, on which the hydroxyapatite coating could be detected. Of course, it was not possible even by this preliminary treatment to apply a continuous coating. FIGS. 4 and 5 show the surfaces of the lasered and hydroxyapatite (HA) coated specimens.

Even though it was possible for the first time to prove the deposition of hydroxyapatite on the roughened surfaces of the aluminum oxide ceramic, the strength of adhesion of the coating was very poor. Quantification of the strength of adhesion was impossible, as was the preparation of a transverse section; the coating fell off immediately. Again, when the raw depth was analyzed it was compared with that of metal materials. With an $R_a$ of 9 μm the raw depth of the TiAl6V4-1 alloy ($R_a \approx 40$ μm) could not be achieved. It was necessary to refrain from any further roughening of the surface in the ceramic substrate, since the aluminum oxide ceramic, unless metallic materials, has an absolute cleavage fracture tendency. If a "predamage" of 40 μm is induced, this "flaw" can trigger breakage. Thus, any further increase of the roughness is impossible from the viewpoint of fracture mechanics.

The present invention is addressed to the problem of making available a method by which ceramic components can reliably be provided with a hydroxyapatite coating.

The problem to which the invention is addressed has been solved by a method with the features of the principal claim. Preferred embodiments are described in the subclaims.

DETAILED DESCRIPTION

Figure 1:
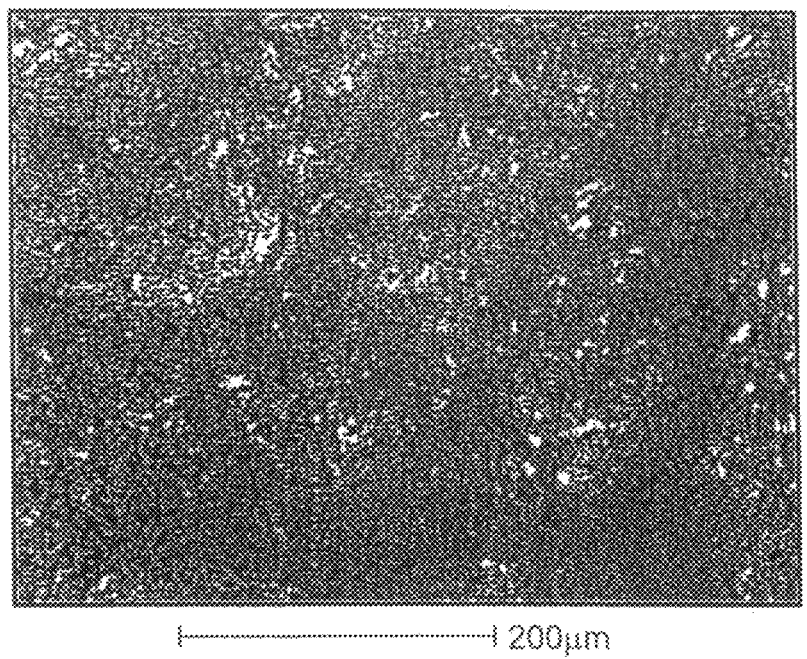
FIG. 1 is an SEM showing a typical surface after laser treatment.
Figure 2:
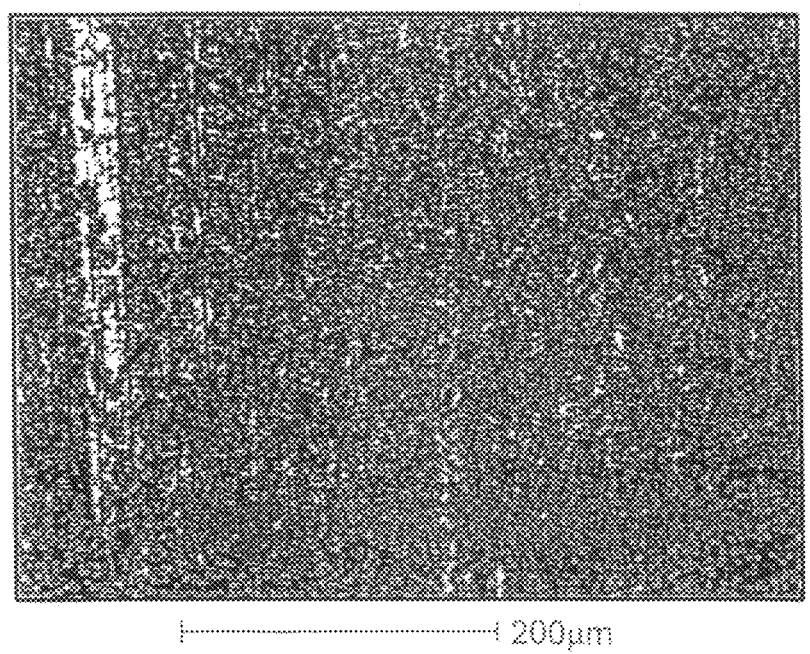
FIGS. 2 and 3 are SEMs showing the surfaces of the lasered and hydroxyapatite coated specimens.
Figure 3:
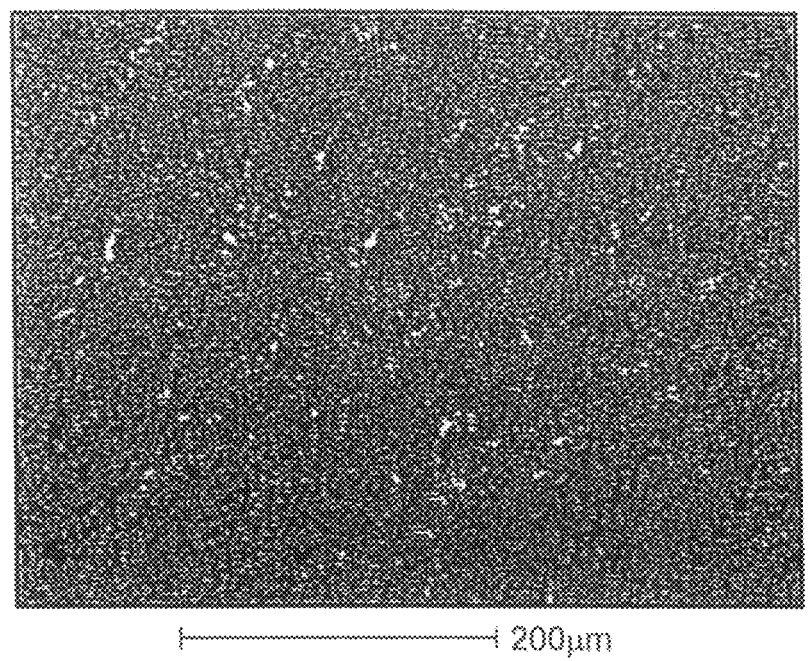
Figure 4:
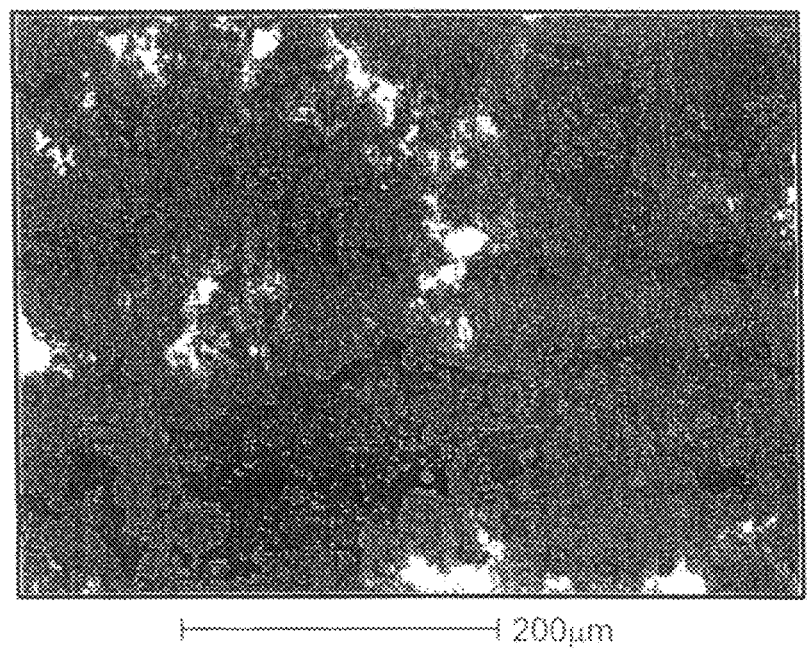
FIGS. 4 and 5 are SEMs showing the transverse section of a lasered end and hydroxyapatite coated specimens.
Figure 5:
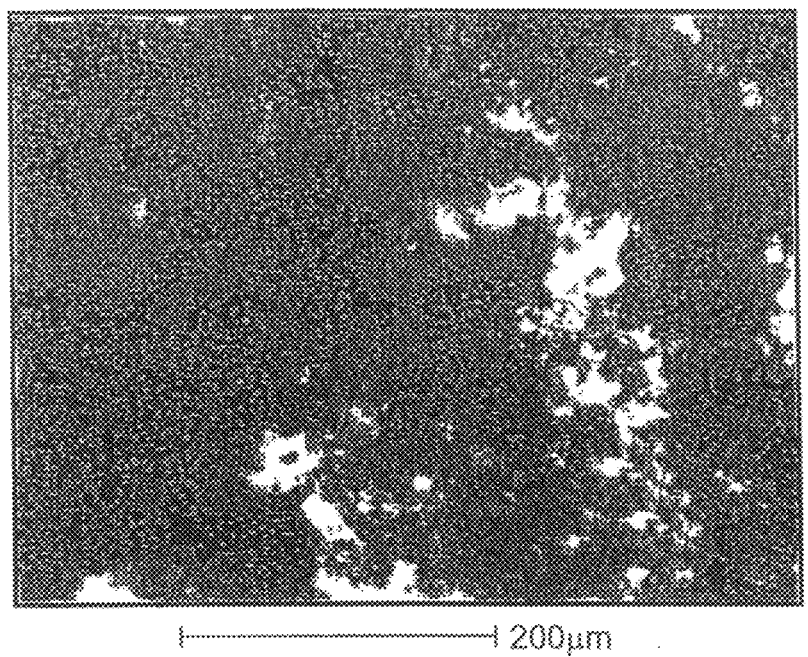

FIG. 1 shows the typical surface after the laser treatment. The entire surface of the aluminum oxide ceramic was then subjected to plasma coating with hydroxyl apatite. For the first time it was possible to detect on this surface a few spots on which the hydroxyl apatite coating could be detected. Nevertheless it was not possible even after this preliminary treatment to apply a continuous coating. FIGS. 2 and 3 show the surfaces of the lasered and hydroxyl apatite (HA) coated specimens.

Surprisingly it was possible according to the invention to coat a ceramic component, preferably a component made of aluminum oxide ceramic, with hydroxyapatite if the surface of the ceramic component is coated with a titanium layer. By the method of the invention it is surprisingly possible for the first time to deposit hydroapatic on the surface of a ceramic component, with sufficient strength of adhesion.

Figure 6:
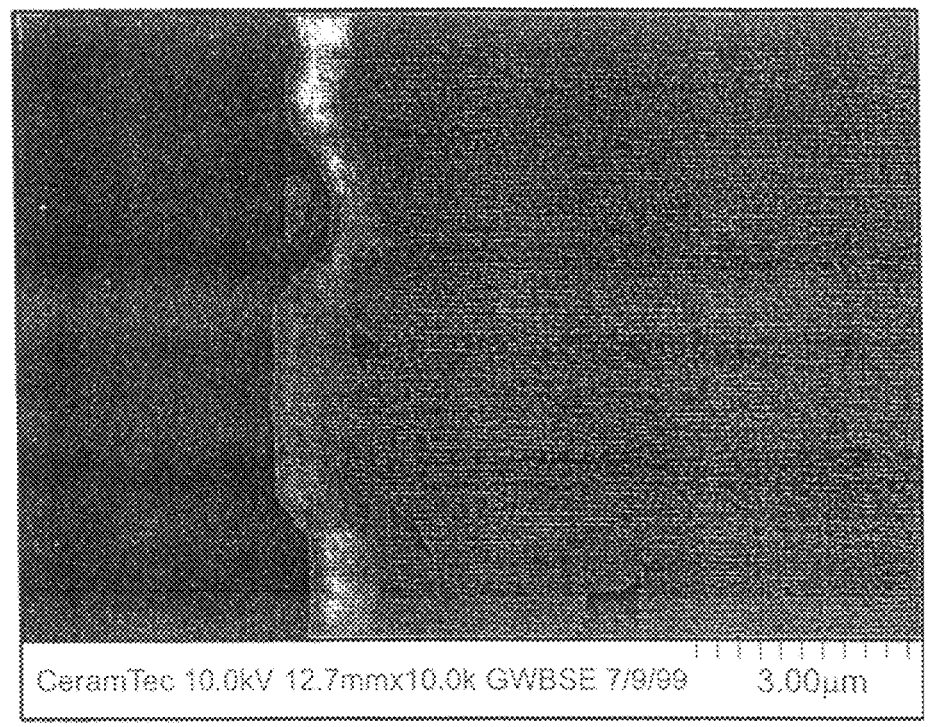
FIG. 6 is an SEM showing the transverse section of a coated specimen.

According to the invention, first ceramic components are provided with a thin titanium coating, for example by PVD (physical vapor deposition). According to the invention, the surface of the ceramic component can be previously roughened, —ground or lasered, for example. The thickness of the titanium layer was about 1 μm; a coating 5 μm thick also led to success. FIG. 6 shows the transverse section of a specimen coated in this manner.

Figure 7:
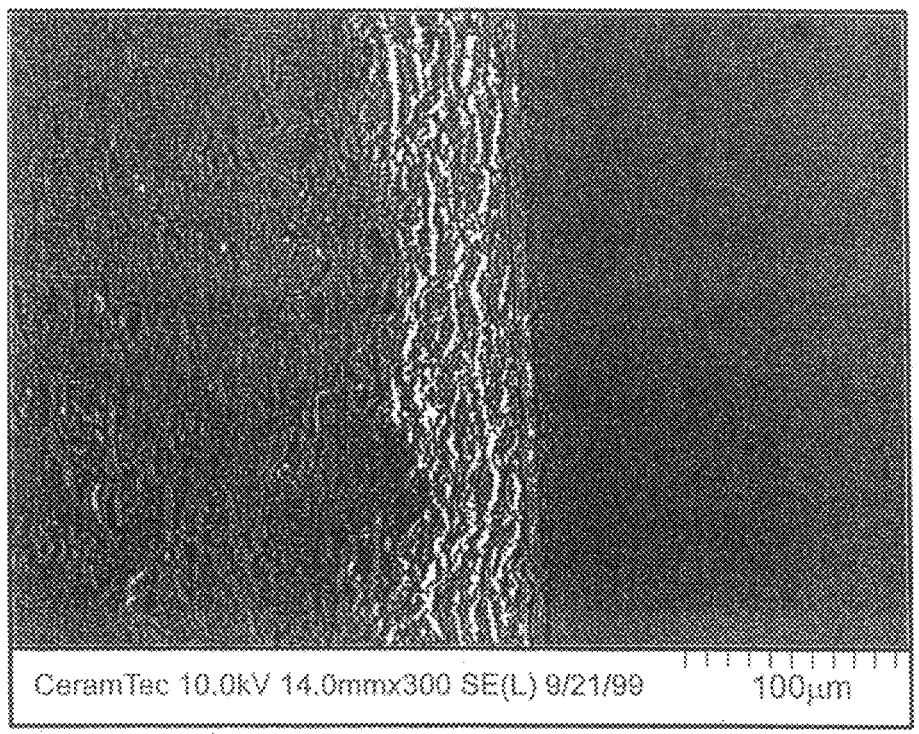
FIGS. 7 and 8 are SEMs showing transverse sections of a hydroxyapatite layer.
Figure 8:
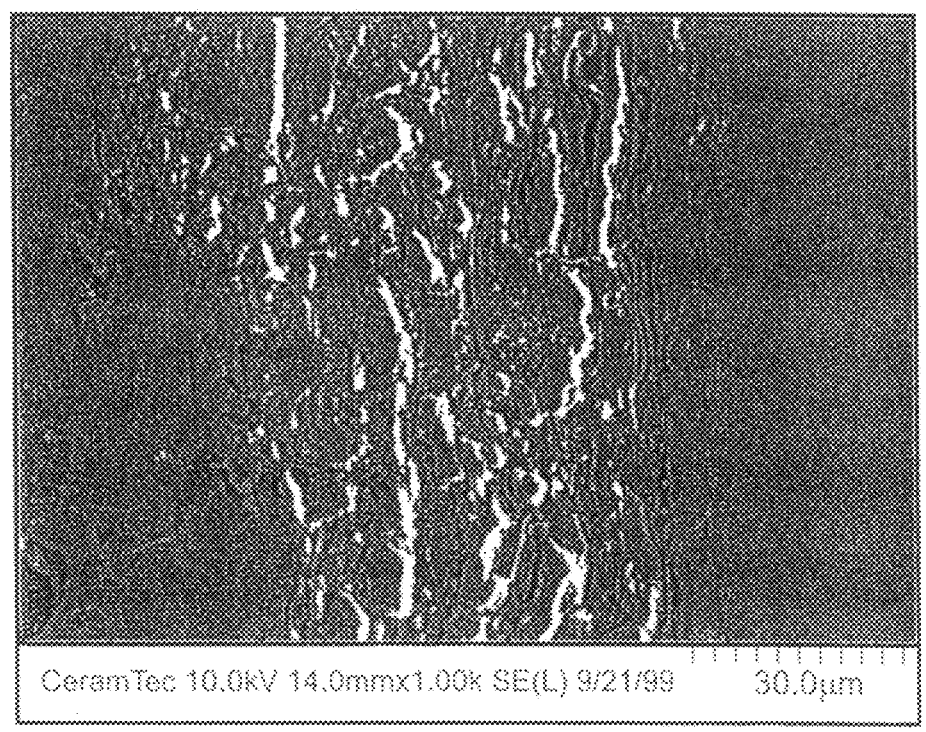

The hydroxyapatite layer was sprayed onto this intermediate layer. The transverse section of this built-up coating is represented in FIGS. 7 and 8 at different enlargements.

Preferably, before the hydroxyapatite is applied by plasma coating, for example, the titanium intermediate layer is subjected also to a sand blasting process to improve adhesion. An especially high strength of adhesion is achieved if the titanium coating is given a roughness of $R_a \approx 40\text{-}50$ μm.

A scratch test on the hydroxyapatite coating confirmed the outstanding strength of adhesion of the coating. Preparation of a transverse section was possible without problems. The measurement of the strength of adhesion was made on five different specimens. The individual values are summarized in Table 1.

TABLE 1

Strength of adhesion of hydroxyapatite on Al₂O₃ with titanium primer

| Specimen | Force [N] | Tension [MPa] |
|---|---|---|
| 1 | 718 | 2.3 |
| 2 | 1203 | 3.8 |
| 3 | 932 | 3 |
| 4 | 1490 | 4.7 |
| 5 | 390 | 1.2 |

From the values obtained by the strength-of-adhesion measurements it can be seen that tensions are surprisingly achieved which are in the range of that of hydroxyapatite coatings on TiAl6V4 alloys.

According to the invention, it is also possible, instead of the conventional titanium intermediate coating, an intermediate coating of the TiAl6V4 alloy can be deposited, for example by the PVD method.

Figure 9:
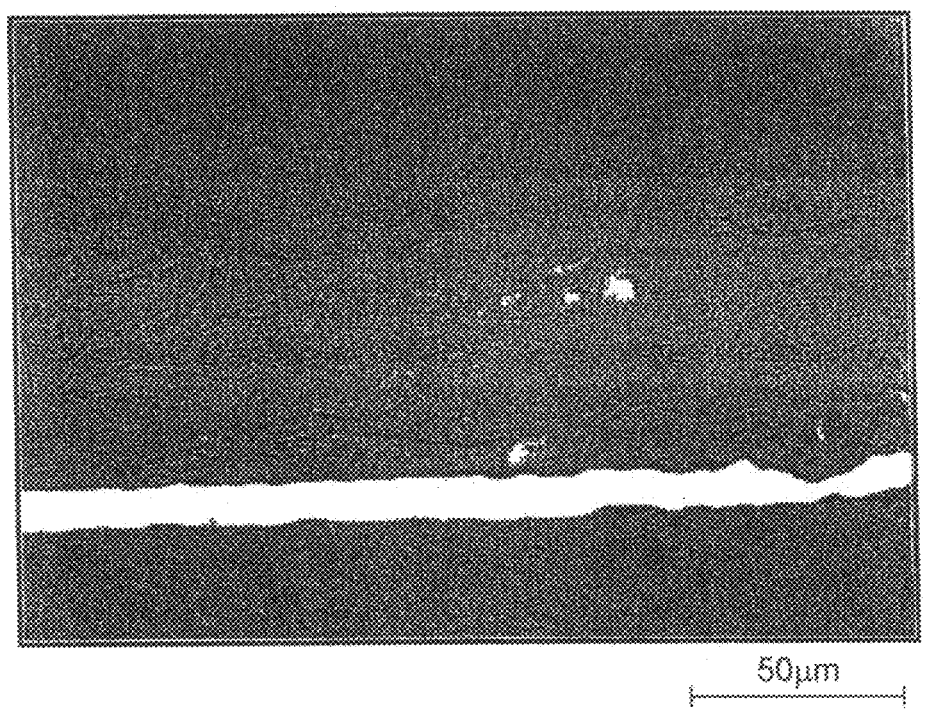
FIG. 9 shows a typical building of layers in the preparation of transverse sections.

FIG. 9 shows the typical building of layers in the preparation of transverse sections. The corresponding strengths of adhesion are listed in Table 2.

| Specimen | Force [N] | Tension [MPa] |
|---|---|---|
| 1 | 582 | 1.9 |
| 2 | 700 | 2.2 |
| 3 | 400 | 1.3 |
| 4 | 498 | 1.6 |

A ceramic component in the form of a cylindrical test specimen was used in the tests. The cylinders, with a diameter of 20 mm and a thickness of 2 mm, were made by the conventional press-turn manufacture as greenbodies, subjected to hot isostatic pressure and annealed. The sintered bodies were then machined with diamond tools to achieve final shape. Other methods for the manufacture of ceramic components can, of course, also be used. Used as the material was a known aluminum oxide material, such as the one known as Biolox® material, for example.

With the present invention it is thus for the first time possible by providing a titanium intermediate coating to deposit hydroxyapatite directly onto ceramic components. The ceramic components that can be made by the method of the invention are also subject matter of the present invention.

Thus, according to the invention, ceramic components can for the first time be made, which can be used for medical purposes, for example as prostheses. Such prostheses display an improved ingrowth characteristic.

The invention claimed is:

1. A method for producing a hydroxyapatite-coated ceramic core component having a Ti-containing layer comprising the steps of:
   coating a ceramic core component comprising aluminum oxide with a titanium-containing layer, wherein the titanium-containing layer comprises at least one of Ti or a TiAl₆V₄-alloy, wherein the titanium-containing layer is up to 5 μm thick,
   subjecting said titanium-containing layer to a sand blasting process to achieve a roughness of $R_a$ 40 to 50 μm, and
   applying hydroxyapatite to the roughened titanium-containing layer to form the hydroxyapatite-coated ceramic component having a Ti-containing layer.

2. A method according to claim 1, wherein the titanium-containing layer is applied by with a physical vapor deposition process.

3. A method according to claim 2, wherein the titanium-containing layer is 1 μm thick.

4. A method according to claim 1, wherein the titanium-containing layer is between 1 and 5 μm thick.

5. A method according to claim 1, wherein the hydroxyapatite is sprayed onto the titanium-containing layer.

6. A method according to claim 1, wherein the ceramic component consists of an aluminum oxide ceramic.

7. A method according to claim 1, wherein the coated ceramic component is in the form of a medical device.

8. A method according to claim 1, wherein the hydroxyapatite-coated ceramic component is a prosthesis.

9. The method of claim 1, wherein the titanium-containing layer comprises the TiAl₆V₄-alloy.

10. A method comprising:
    coating a ceramic component comprising at least one titanium-containing layer, wherein the titanium-containing layer comprises titanium or TiAl₆V₄-alloy and wherein the titanium-containing layer is up to 5 μm thick;
    adjusting the titanium-containing layer by roughening to a roughness of $R_a$ 40 to 50 μm to form a roughened titanium-containing layer, wherein said roughening is conducted by sandblasting; and
    applying hydroxyapatite to the roughened titanium-containing layer to form a hydroxyapatite-coated ceramic component.

11. The method of claim 10, wherein the hydroxyapatite is applied by chemical vapor deposition.

12. A method according to claim 10, wherein the coated ceramic component is formed as a medical device.

13. A method comprising the steps of:
    coating a ceramic component, wherein the ceramic component comprises aluminum oxide, with a titanium-containing layer which is up to 5 μm thick, wherein the titanium-containing layer consists of at least one member selected from the group consisting of Ti or a TiAl₆V₄-alloy,
    sandblasting the titanium-containing layer to achieve a roughness of $R_a$ 40 to 50 μm to form a roughened titanium-containing layer, and
    applying hydroxyapatite to the roughened titanium-containing layer to form a hydroxyapatite-coated ceramic component.

* * * * *